United States Patent
Jokinen

(10) Patent No.: US 8,418,927 B2
(45) Date of Patent: Apr. 16, 2013

(54) OFF-LINE RESPONSE CARD AND ARRANGEMENT FOR ENQUIRING A RESPONSE FROM THE RESPONSE CARD

(75) Inventor: Tapio Jokinen, Espoo (FI)

(73) Assignee: Medixine Oy, Espoo (FI)

( * ) Notice: Subject to any disclaimer, the term of this patent is extended or adjusted under 35 U.S.C. 154(b) by 224 days.

(21) Appl. No.: 12/735,301

(22) PCT Filed: Dec. 30, 2008

(86) PCT No.: PCT/FI2008/050792
§ 371 (c)(1),
(2), (4) Date: Jun. 29, 2010

(87) PCT Pub. No.: WO2009/083654
PCT Pub. Date: Jul. 9, 2009

(65) Prior Publication Data
US 2010/0283233 A1    Nov. 11, 2010

(30) Foreign Application Priority Data
Dec. 31, 2007 (FI) .................................. 20071030

(51) Int. Cl.
*G06K 19/06* (2006.01)
(52) U.S. Cl.
USPC .................................................. 235/492

(58) Field of Classification Search ............ 235/492
See application file for complete search history.

(56) References Cited

U.S. PATENT DOCUMENTS

| 6,085,752 A * | 7/2000 | Kehr et al. ............... 128/897 |
| 8,066,192 B2 * | 11/2011 | Maus ........................ 235/492 |
| 2004/0053648 A1 * | 3/2004 | Gremo et al. ........... 455/575.1 |
| 2006/0285736 A1 | 12/2006 | Brown |

FOREIGN PATENT DOCUMENTS

| EP | 1006982 | 6/2000 |
| EP | 1115363 | 7/2001 |
| GB | 2436160 | 9/2007 |

* cited by examiner

*Primary Examiner* — Kristy A Haupt
(74) *Attorney, Agent, or Firm* — Ware, Fressola, Maguire & Barber LLP

(57) ABSTRACT

An off-line response card having a plurality of sensors is provided with a replaceable cover, where the cover is provided with a plurality of questions and choices for questions. The choices are arranged into the cover so that each choice corresponds to one sensor in the response card when the cover is placed on the response card. The sensor is adapted to sense whether the choice in the cover is influenced (selected) and output identifying information of said sensor as a result of the influence.

13 Claims, 1 Drawing Sheet

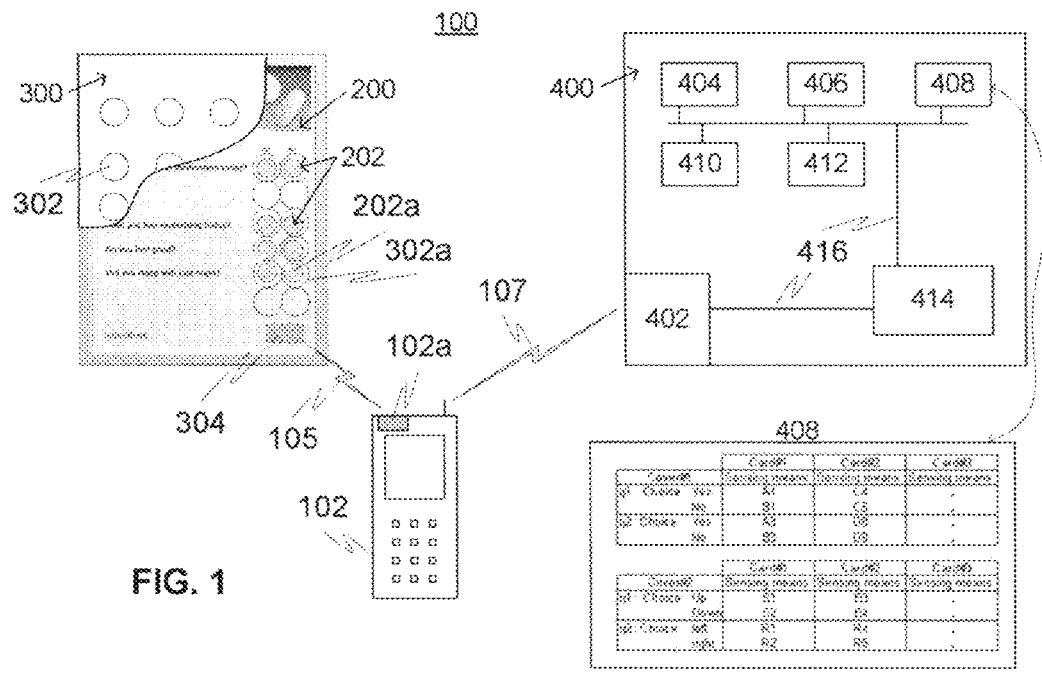
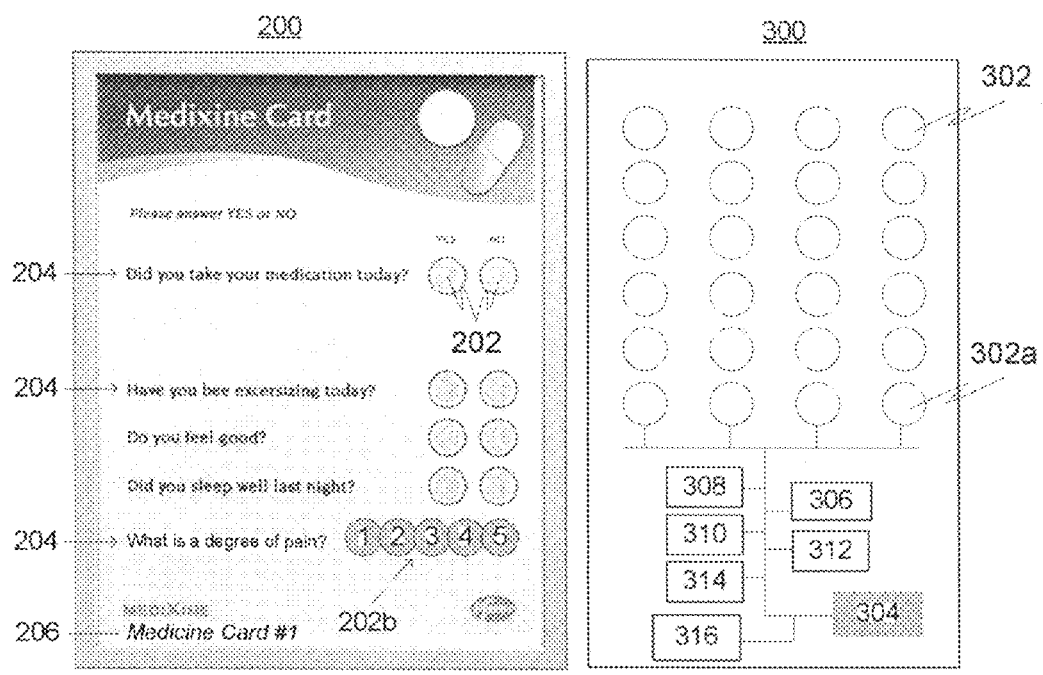

OFF-LINE RESPONSE CARD AND ARRANGEMENT FOR ENQUIRING A RESPONSE FROM THE RESPONSE CARD

CROSS REFERENCE TO RELATED APPLICATIONS

This application is the U.S. National Stage of International Application Number PCT/FI2008/050792 filed on Dec. 30, 2008 which was published in English on Jul. 9, 2009 under International Publication Number WO 2009/083654.

TECHNICAL FIELD OF THE INVENTION

The invention relates to an off-line response card and arrangement for enquiring a response from the response card.

BACKGROUND OF THE INVENTION

Different kinds of enquiries are sent nowadays to users for enquiring as to their opinions about certain event or experiences, such as asking their opinions about medicines and asking their feelings or conditions after intake of medicines and possible effects of medicines. Often used methods of a prior art includes e.g sending SMS enquiries or enquiries via internet or email, where the user should use either modern mobile terminals and phones or computers. However, often those users are elder people who are not familiar with technical devices and are not able to use those apparatuses, or even have none. In addition one problem is that often elder people cannot remember to answer separately to questions after they have taken their medicines, for example.

Some solutions are known from a prior art to follow e.g. medicament dispense or asking some questions. EP 1 006 982 B1 describes a medicament dispense sensing device solution, where sensing elements detect when the medicament is dispensed and an electronic unit registers this with time indication. In addition EP 1 115 363 B1 describes a response form comprising an answer field including questions to enquiry e.g. opinions and corresponding input means for incurring electrical signal to be registered by an electric unit as a response to the question.

The known prior art solutions have, however, some drawbacks, namely typically those response cards are disposable, thus increasing waste of materials. In addition the response cards are prepared for a certain use known beforehand, which make the use of them clumsy, namely one should know beforehand how many response cards (s)he need for a first use, and how many cards another use, for example.

SUMMARY OF THE INVENTION

An object of the invention is to offer a solution for enquiring (requesting) a response from users in an easy and effective way so that any conventional expensive computers or mobile phones are not needed to answering queries, but still the answers can be gathered and analysed in an accurate way. In addition an additional object of the invention is to provide a response form, which can be used for numerous different purposes so that the final use can be decided even if only just the response form is taken into the use.

According to an embodiment of the invention the off-line response card comprises an inexpensive base having plurality of sensors, such as electrical sensors implemented by capacitive or resistors, for example, sensing whether they are influenced for example by a finger. The sensors are identifiable so that afterwards it can be determined which sensors were influenced.

According to an embodiment of the invention a plurality of replaceable covers are provided with a plurality of questions and corresponding choices so that at least one choice relates to one question. The covers and questions in the covers may relate e.g. to enquiring (requesting) opinions about certain event or experiences, such as asking user opinions about medicines and feelings or conditions after intake of medicines and possible effects of medicines. However, the invention does not limit only the medical related questions, but using different questions in the cover every kind of opinions can be asked.

In an embodiment of the invention the response card is provided with the replaceable cover so that each choice corresponds to one sensor in the response card when the cover is placed on the response card. Now when the choice in the cover is selected the corresponding sensor in the response card advantageously determines the influence or selecting. After determining the selection of a certain choice the corresponding sensor, the card outputs an electrical signal as a result of the selection. The electrical signal is according to an embodiment of the invention identifyinq information of said sensor. However, the signal may also be another electrical signal, such as a voltage pulse, and the identity of said sensor is determined otherwise. The response card may advantageously determine said output and store information that a certain sensor (actually a corresponding choice in the cover) is selected. In an embodiment it is enough to store only said identifying information of the influenced sensor.

The response card may also comprise a memory to store information, where the memory is readable outside the response card. In an embodiment the memory is either implemented by an RFID or the memory is in data communication with an RFID so that the memory can be read outside e.g. with an RFID reader. In this way the technological structure of the response card can be kept simple and also inexpensive.

In addition to keep the response card's technological structure simple and inexpensive, stored information is advantageously analysed outside the response card. For example, information stored by the response card is read outside by an RFID reader and delivered to an exterior analyzer of the response card, which may be implemented for example with a server being in data communication connection with the RFID reader. In an embodiment the RFID reader may be either in data communication with a communication unit, such as a mobile phone, computer or other communication terminal, or the RFID reader is integrated with the communication unit, such as the mobile phone, computer or other communication terminal.

According to an embodiment of the invention the cover (or at least the type of the cover) is provided with unique ID information identifying said cover. In an embodiment the questions and especially choices and their placement can be determined based on ID information of the cover or at least cover type. Again it can be determined based on the cover's ID information and placing of the sensor in the response card which choice of the cover falls to which sensor in the response card, when said cover is placed on the response card. In an embodiment all response cards have similar structure and sensors in every response card are placed similarly, whereupon no special information about the response card used is needed.

However, in another embodiment of the invention response card (or at least the type of the response card) may be provided with unique ID information identifying the response card used. Said ID information of the response card may be stored for example in connection with the memory or RFID advantageously so that it cannot be copied or changed. In an embodiment unique ID information of the response card may also be used for identifying a user of the card. However, in an embodiment the response card may be provided also with information of a user, such as information relating to user's patient data, social security number, and medication.

In an embodiment, where the response cards are structurally identical, it is enough to deliver only identifying information of the influenced sensor and ID information of the used cover to the exterior analyzer, whereupon the analyzer can determine at first which cover (or cover type) has been used and at second based on identifying information of the influenced sensor which choice of the cover has been selected.

However, if there are also a plurality of response cards used, then also information identifying the used response card should be delivered to the analyzer so that the analyzer can be sure e.g. of the placing of the sensor in the response card, or even be secured about the user of the card.

In an embodiment of the invention the response card sends ID information of the response card to said RFID-reader, when stored information is read. In an embodiment, also ID information of the used cover is delivered at the same time to the analyzer when stored information is read. However, this is optional.

Now, when the exterior analyzer knows the used cover, it can determine the choices for each questions used in said cover. In addition the exterior analyzer knows based on the cover information the placing of the choices and based on information of the used response card also the placing of the sensor, whereupon it also can determine which choice corresponds which sensor. Now, when the exterior analyzer are provided with ID information of used cover and ID information of influenced sensor, the analyzer can determine which choices have been selected by the user and again form response information based on said determined choices of the used cover.

In addition according to an embodiment the response card comprises a time stamping unit for time stamping stored information. Now, for example when the memory of the response card is read only a few times in a week or month, or even in a year, the events (e.g. identifying information of the influenced sensor) may be stored into the memory with a time stamp so that also the instant of each event can be determined afterwards if needed.

In addition the response card may be provided with reminders so that the user can be reminded to answer to the query. Reminders can be separate for each user, such as a patient. Furthermore stored information and/or information to be delivered may be encrypted so that it cannot be manipulated or stolen over the internet, for example. The encryption method used may be e.g. a 128 bit AES encryption method.

According to the invention it is possible to use one response card as a base for different types of covers dedicated for different types of questions or enquiries, such as enquiring information about effects of used medicine, therapy or treatment, opinion about an event, such as TV show, movie, competition, and feeling of a patient for example after medical operation or after taking medicine. In addition the response card may be used for example for a viva voce, evaluation a movie, or for any evaluation of a service event, such as restaurant service or fare.

Especially it should be noted that the final use of the response card can be decided even only just when the response card is taken into the use, because the purpose of used can be selected by choosing the cover in an appropriate way. Furthermore, by using replaceable covers the use of response card is hygienic even if it is reused.

The exemplary embodiments of the invention presented in this document are not to be interpreted to pose limitations to the applicability of the appended claims. The verb "to comprise" is used in this document as an open limitation that does not exclude the existence of also unrecited features. The features recited in depending claims are mutually freely combinable unless otherwise explicitly stated.

BRIEF DESCRIPTION OF THE DRAWINGS

Next the invention will be described in greater detail with reference to exemplary embodiments in accordance with the accompanying drawings, in which FIG. 1 illustrates an exemplar arrangement for enquiring response information from a user using a response card according to an advantageous embodiment of the invention, FIG. 2 illustrates an example of a cover used in a response card according to an advantageous embodiment of the invention, and FIG. 3 illustrates an example of a response card according to an advantageous embodiment of the invention.

DETAILED DESCRIPTION

FIG. 1 illustrates an exemplar arrangement 100 for enquiring (requesting) response information from a user using a response card 300 according to an advantageous embodiment of the invention. The response card 300 can be provided with the replaceable cover 200 so that each choice 202 corresponds with one sensor 302 in the response card 300 when the cover 300 is placed on the response card 200. For example the choice 202a (No) for the last question (Did you sleep well last night?) in the cover 200 corresponds with the sensor of 302a of the response card, when the cover is placed on the response card.

Now when for example the choice 202a in the cover 200 is selected, the corresponding sensor 302a in the response card 300 determines the influence or selecting. After determining the selection of a certain choice 202a the corresponding sensor 302a outputs an electrical signal as a result of the selection, whereafter said signal is stored in a memory of the response card. The memory may be read outside the response card for example via an RFID 304 and communication link 105 by an RFID reader 102a, which may be integrated into a mobile phone 102, for example. When stored information has been read, information is delivered to an analyzer 400, which may be a server, for example. The analyzer 400 then determines the response based on received information, such as based on received identifying information of the sensor influenced as well as identifying information of the used cover type, whereupon the analyzer can determine which choice of the used cover type corresponds with which sensor.

In this example the user has selected for example a choice 202a "No" for a question "Did you sleep well last night?", whereupon identifying information of the sensor 302a has been delivered to the analyzer, because the sensor 302a corresponds with the choice of 202a in the cover 200. In addition the analyzer 400 is also provided with identifying information of the used cover, like Medicine card #1, whereupon the analyzer knows the location of each choice 202 on the cover 200, and is thus able to determine the location of each choice 202 on the response card 300 as well as the corresponding sensor 302. Thus the analyzer is in this example able to determine based on identifying information of sensor 302a and identifying information of the used cover (Medicine card #1) that user has selected the choice 202a, which is an answer to the last question "Did you sleep well last night?". The analyzer can be adapted to form different kinds of conclusions of responses, like trend or numbers of Yes/No—answers, for example.

FIG. 2 illustrates an example of a replaceable cover 200 used in a response card 300 according to an advantageous embodiment of the invention. The cover is provided with a plurality of questions 204 and choices 202 so that at least one choice relates to one question. The cover 200 may also be provided with a sliding scale choice 202b, where the user can select the choice for example in a scale from 1 to 5. The corresponding question may be e.g. "What is a degree of pain?".

According to an embodiment the cover is provided with unique ID information identifying said cover 200 or at least the type of the cover 200, such as "Medicine card #1" 206 referring to the first type of card relating to medicine. In an embodiment the questions and especially choices and their placement can be determined based on the cover's ID information.

The cover material may be e.g. an adhesive label onto which the questions and choices are printed. However, also other kind of cover material can be used.

FIG. 3 illustrates an example of a response card 300 according to an advantageous embodiment of the invention, where the response card 300 comprises a plurality of identifiable sensors 302 each of which is adapted to sense whether the choice in the cover corresponding with said sensor is influenced and output identifyinq information (such as 302a) of said sensor as a result of the influence. The response card 300 comprises a determination unit 306 for determining said output and memory 308 for storing said identifying information of the influenced sensor. The memory 308 are readable outside the response card 300 advantageously via an RFID 304 of the response card.

In an embodiment the response card 300 may be provided with unique ID information identifying the response card 300 (such as RC#1) or at least the type of the response card 300, especially if there are a plurality of different kinds of response cards, or otherwise if the response card used should be identified. Said ID information of the response card may be stored for example in connection with the memory or RFID.

In addition the response card 300 may comprise a time stamp unit 310 for time stamping stored information. Furthermore the response card 300 may also comprise a reminder unit 312 for reminding the user for example to answer the query once a day. Furthermore the response card 300 may also comprise an encryption unit 314 for encrypting information (stored or delivered).

Furthermore the response card 300 may comprise a power source 316 for feeding energy to different units in the response card needing power, as well as a wiring to connect appropriate units to each other in an appropriate way.

In addition relating to FIG. 1, an example of an analyzer 400 used for analysing response information from a response card 300 is described next in more details. The analyzer, such as a server, comprises receiver 402 for receiving information from the RFID reader via a communication connection 107 (illustrated in FIG. 1). The analyzer comprises also a determining unit 404 for determining a cover used and a sensor determining unit 406 for determining the influenced sensor based on identifying information of said influenced sensor delivered to the analyzer.

Advantageously the analyzer comprises a database 408, such as a table, comprising information relating to possible covers (or cover types), such as "Cover #1" in table #A, choices of the cover, such as "Yes" and "No" and corresponding sensor, such as "A1" and "B1". In addition the table may also comprise information about the questions so that for question "q1" there are two choices "Yes" and "No" and the sensor A1 in card#1 corresponds with "Yes" for the question "q1" in the cover "Cover1", and the sensor B1 in card#1 corresponds with "No" for the question "q1" in the cover "Cover1".

Furthermore the table may also comprise information about different types of response cards, so that the sensor A1 in card#1 corresponds with "Yes" for the question "q1" in the cover "Cover1", but the sensor C4 corresponds with "Yes" for the question "q1" in card#2 for the cover "Cover1".

The analyzer comprises a choice determining unit 410 using the above mentioned database or table for determining the choices for each questions used in each cover, as well as a placing of the choices and based on information of the used response card also the placing of the sensor (optional), determining which choice corresponds with which sensor, and determining which choices have been selected by the user. The analyzer may also comprise a forming and outputting response unit 412 for forming and also outputting response information based on said determined choices of the used cover.

Advantageously the analyzer comprises a data analysing unit 414, such as a processor for processing data and controlling function of the means of the analyzer and data flow between the units via a data bus 416. In addition data operations and determining operations are advantageously implemented by a computer program product run on the analyzer.

The invention has been explained above with reference to the aforementioned embodiments, and several advantages of the invention have been demonstrated. It is clear that the invention is not only restricted to these embodiments, but comprises all possible embodiments within the spirit and scope of the inventive thought and the following patent claims.

The invention claimed is:

1. An off-line response card, comprising
   a plurality of identifiable sensors,
   wherein
      the card is configured to receive a physical cover having printed indicia thereon, said cover being provided with a plurality of questions and at least one choice for each question, where choices are arranged into the cover so that each choice corresponds to one sensor in the response card when the cover is placed on the response card,
      each of the identifiable sensors is configured to sense whether the choice in the cover corresponding to said sensor is selected and to output an electrical signal as an information of the selection, and
      the off-line response card is configured to determine and store said output electrical signal without contemporaneous communication to another device.

2. The off-line response card of claim 1, wherein said output electrical signal is identifying information of said sensor.

3. The off-line response card of claim 1, wherein unique ID information identifying said response card is connected to said response card.

4. The off-line response card of claim 1, wherein the card comprises a means for time stamping information to be stored.

5. The off-line response card of claim 1, wherein the card comprises an RFID configured to be readable outside by an RFID-reader and send stored information via an RFID-connection established between said RFID-means and RFID-reader to said RFID-reader.

6. The off-line response card of claim 5, wherein the card is configured to send said unique ID information identifying the response card to said RFID-reader.

7. The off-line response card of claim 1, wherein the card is configured to be configurable by information of a user, including information relating to user's patient data, social security number, and medication.

8. The off-line response card of claim 1, wherein the cover comprises a unique ID identifying a cover type, and identifiable questions and choices.

9. The off-line response card of claim 8, wherein the cover type is used for enquiring information relating to intake or effects of medication, therapy or treatment, feeling of a patient, or opinion about an event or evaluation.

10. A system for enquiring response information from an off-line response card, wherein said off-line response card comprises a plurality of identifiable sensing means,
and wherein
the card is configured to receive a physical cover having printed indicia thereon, said cover being provided with a plurality of questions and at least one choice for each question, where choices are arranged into the cover so that each choice corresponds to one sensing means in the response card when the cover is placed on the response card,
each of the identifiable sensing means is configured to sense whether the choice in the cover corresponding to said sensing means is influenced and to output an electrical signal as an information of the influence, and
the off-line response card is configured to determine and store said output electrical signal without contemporaneous communication to another device, wherein
the system comprising a server and reader for reading information identifying the influenced sensor from the response card and sent to said server via a connection established between said reader and server.

11. The system of claim 10, wherein
said server is provided with unique ID information identifying said response card,
said server is provided with identifying information of a sensor of said response card,
said server is provided with unique ID information identifying said cover type used on the response card as well as information about which choice of said cover having said unique ID information that corresponds to which sensor of a card having said unique ID information when said cover type is placed on the response card,
whereupon said system is configured to determine selected choices of said cover used on said response card based on determined identifying information of the sensor, and thereby configured to form response information based on said determined choices of said cover.

12. The system of claim 10, wherein the card comprises an RFID configured to being read outside by an RFID-reader and send stored information via an RFID-connection established between said RFID and RFID-reader to said RFID-reader.

13. The system of claim 10, wherein the card is configured to send said unique ID information identifying the response card to said RFID-reader.

* * * * *